United States Patent [19]
Friedli et al.

[11] Patent Number: 6,106,498
[45] Date of Patent: Aug. 22, 2000

[54] DISPOSABLE CASSETTE FOR CONNECTION TO A LIQUID DRUG INFUSION PUMP

[75] Inventors: Kurt Friedli, Lyssach, Switzerland; James G. Skakoon, St. Paul, Minn.

[73] Assignee: Disetronic Licensing AG, Switzerland

[21] Appl. No.: 08/981,329

[22] PCT Filed: Jul. 6, 1995

[86] PCT No.: PCT/EP95/02632

§ 371 Date: Mar. 18, 1998

§ 102(e) Date: Mar. 18, 1998

[87] PCT Pub. No.: WO97/02059

PCT Pub. Date: Jan. 23, 1997

[51] Int. Cl.[7] ............................. A61M 1/00; A61M 5/00
[52] U.S. Cl. ............................ 604/153; 604/247
[58] Field of Search ............................ 604/65, 67, 131, 604/153, 189, 246, 247, 256; 128/DIG. 12; 417/477.9, 477.2, 474, 63, 479

[56] References Cited

U.S. PATENT DOCUMENTS

| | | | |
|---|---|---|---|
| 4,537,561 | 8/1985 | Xanthopoulos | 417/63 |
| 4,712,583 | 12/1987 | Pelmulder et al. | 137/852 |
| 4,758,228 | 7/1988 | Williams | 604/153 |
| 4,878,896 | 11/1989 | Garrison et al. | 604/65 |
| 5,006,110 | 4/1991 | Garrison et al. | 604/65 |
| 5,213,573 | 5/1993 | Sorich et al. | 604/66 |
| 5,308,333 | 5/1994 | Skakoon | 604/126 |
| 5,403,277 | 4/1995 | Dodge et al. | 604/30 |

*Primary Examiner*—Wynn Wood Coggins
*Assistant Examiner*—Michael J. Hayer
*Attorney, Agent, or Firm*—Dorsey & Whitney LLP

[57] ABSTRACT

The disposable cassette for use with a liquid drug infusion pump comprises a cassette body (1) with a flexible pump tube (2) between an inlet (3) for connection to a drug reservoir on the upstream side and an outlet (4) for delivery of the drug to a medical patient on the downstream side; a pressure detector membrane (18) operatively connectable to said infusion pump having means to measure the pressure in the fluid circuit of the cassette; a passive valve (7) having a pre-stress producing a forward opening pressure of at least 0.15 bar, and an optical code (6) located on the cassette body (1) for recognition of the cassette by said infusion pump.

32 Claims, 6 Drawing Sheets

DISPOSABLE CASSETTE FOR CONNECTION TO A LIQUID DRUG INFUSION PUMP

RELATED APPLICATIONS

This application claims the priority of PCT Application No. PCT/EP95/02632, filed Jul. 6, 1995, which is incorporated herein by reference.

SUMMARY OF THE INVENTION

This invention relates to a disposable cassette for use with a liquid drug infusion pump according to the preamble of claim 1.

There is significant need for infusion devices to deliver therapeutic medicaments to patients. There has been and continues to be several important trends in the field of infusion therapy. Among these are the need for greater safety as the therapies and drugs evolve, the combination of ever more therapeutic capabilities into one infusion device, the desire to lower operation costs the inclusion of ever more functional features into the devices, and the increasing use of ambulatory and home therapy methods.

The prior art devices exhibit a number of weaknesses and lack a number of features, all of which contribute to being less than optimal devices for their intended purpose.

For example, some devices exhibit an unsafe failure mode called free flow. In this situation, the drug reservoir is above the patient and, due to this reservoir elevation, the drug flows uncontrolled into the patient resulting in an overdose. The usual causes of this condition are pumping mechanism failures or, more often, inadvertent removal of the cassette from the pump. Measures used in previous devices to minimize this problem are warning labels, alarms, and normally closed active valves (e.g. pinch valves) that are activated only by the pump.

In the past it has also been necessary to have a variety of different pumps, each with different therapeutic capabilities. This brings with it higher costs, more extensive personnel training, logistics problems, and the like. One major reason for this is the extremely wide range of infusion rates necessary to accomplish all the common therapies. Such a wide range is difficult to obtain in a single device without compromising one or the other therapies for such factors as accuracy, continuity of flow, battery life (if battery operated), and so on.

Most modern infusion pumps are capable of detecting an occlusion of the patient's IV line. Typically, these are pressure detectors with a preselected trip point which cause an alarm. These function adequately to detect an occlusion down line from the pump. The detection of an occlusion up line of the infusion pump is more difficult to accomplish and is done in the prior art by use of a drip chamber and drop sensor, both of which add cost and inconvenience to the devices. Further, such drop sensors are wholly unsuitable for ambulatory use.

A number of techniques are employed to sense pressure in the infusion line and are well known in the art. Nevertheless, existing systems compromise performance parameters such as reliability, accuracy, sensitivity, and repeatability against the production costs of the infusion pump and disposable cassette.

Many infusion pump cassettes and most ambulatory infusion pump cassettes have a flexible tube which is squeezed by the pumping mechanism to effect a peristaltic or displacement pumping action. These tubes must have special characteristics to be suitable for this use, which characteristics then make them difficult to reliably bond to the other cassette components. Such difficulties result in either increased assembly costs, leaking bond joints, or both. Further, the infusion rate accuracy is related to the accuracy of the internal diameter. Because these tubes are fabricated by extrusion, which is relatively inaccurate, production costs increase due to inspection and culling procedures.

Passive check valves are known in the prior art, including those that have a positive forward crack pressure, examples of which are disclosed in U.S. Pat. No. 4,856,340 to Garrison, U.S. Pat. No. 4,646,781 to McIntyre, et al., and U.S. Pat. No. 4,535,820 to Raines, et al. If constructed to have the correct range for forward crack pressure, they can be used to prevent free flow due to reservoir/patient elevation differences. Nevertheless, prior art valves often require costly inspection and culling procedures due to part and assembly process variability. For example, the housings of such valves are typically ultrasonically welded together. The assembled position of the parts after welding can be dependent on the parameters of the welding process. Thus, variability in the welding process can affect the final part positions and, in turn, the crack pressure accuracy substantially enough to leave it outside the performance requirements.

From the U.S. Pat. No. 4,712,583 PELMULDER ET AL. a passive valve for medication infusion systems is known which opens when a minimal pressure drop occurs across it. This back check valve is designed therefore to prevent reverse flow, this making it useful for construction of a pump with two such valves with a piston. This type of valve, however, cannot solve the problem of preventing forward flow up to a certain pressure drop.

Several physical principles are in common use to detect air in the fluid path of disposable cassettes and thereby to prevent dangerous infusion of air. The most common are ultrasonic transducers and optical sensors. Many of the optical methods use the principle of total reflection at an interface between materials of dissimilar densities, in this case air and plastic. Examples of such systems are disclosed in U.S. Pat. No. 4,884,065 to Crouse, et al. and U.S. Pat. No. 5,006,110 to Garrison, et al. Prior art total reflection optical systems, although functionally effective, are neither fail safe nor failure testable, meaning that a component failure results in an unsafe failure mode.

Prior art devices also have weaknesses regarding ease of use, particularly regarding assembly of the cassette onto the pump in the proper position. Problems such as complicated, multiple step procedures and unsure or insecure positioning are common.

From WO93/04285 ABBOTT LAB. a method for monitoring fluid flow from a volumetric pump is known having a flexible tubing with a pressure sensing means.

From U.S. Pat. No. 5,078,683 SANCOFF a programmable infusion system is known which discloses an optical bar code label attached to the source of intravenous fluid, such as a bag.

Disposable cassettes for use with infusion pumps have in the past been costly and troublesome to produce. Because of ever more price pressure, these high costs and production difficulties are increasingly unacceptable.

The invention as claimed aims at solving the above described problems by providing a disposable cassette for use with a liquid drug infusion pump with a passive anti-free-flow valve, which provides significant improvements and advantages over the prior art.

The invention as claimed aims at solving the above described problems by providing a disposable cassette for use with a liquid drug infusion pump with a passive anti-free-flow valve, which provides significant improvements and advantages over the prior art.

The disposable cassette has an inlet for connection to a drug reservoir, an outlet for connection to the patient, a flexible pump tube, and a cassette body. The flexible pump tube, together with the tube squeezing mechanism of the infusion pump, comprises the method of pumping the medicament to the patient. The cassette body has a flexible pressure detector interface membrane, a passive check valve with a positive forward opening pressure to prevent free flow, an optical code to allow the infusion pump to correctly identify the cassette, and an optical air detector chamber readable by the infusion pump. The cassette body snaps into the infusion pump and is held in proper alignment by cooperative mechanical function between the cassette body and the infusion pump.

A pressure detector in the infusion pump measures pressure in the infusion line through the pressure detector interface membrane of the cassette. The pressure measurement is used to detect an occlusion of the infusion line. The pressure detector interface membrane is a thin, flat, flexible disk that isolates the sterile fluid path of the cassette from the non-sterile pressure sensing detector of the pump and allows the pressure in the fluid path to be faithfully transmitted to the infusion pump's pressure detector.

The passive check valve in the cassette has a pre-stress producing a forward opening pressure that is greater than the typical elevation of the drug reservoir above the patient. Thus, the possibility of harmful uncontrolled free flow to the patient is avoided. Further, this valve prevents reverse liquid flow under all circumstances. Thus, due to the specific arrangement of the cassette's functional items, an under-pressure develops when the infusion line is occluded on the inlet side. In turn, this under-pressure is recognizable by the pressure detector as an occlusion of the inlet side.

An optical code on the cassette body is read by optical sensors in the infusion pump. By reading this code, the pump is able to automatically determine which cassette has been installed and to adjust certain parameters to match the cassette. This easily and safely allows the use of different cassettes in the same pump to give, for example, different flow rate ranges. This code and sensor system also serves to determine that the cassette has been properly installed.

The optical air detector chamber of the cassette is read by a system of optical source and sensors to determine the presence of air or liquid in the chamber. It is used to avoid harmful infusion of air into the patient. The system has dual complementary channels to produce positive independent signals for either air or liquid thus allowing automatic safety testing for failures.

The cassette body has plateau surfaces which mate with hooks on the infusion pump. A spring action passively forces the cassette into the proper relationship between the plateaus and hooks during insertion of the cassette body into the infusion pump. Actively overcoming the spring action by hand allows easy removal of the cassette body from the pump.

By embodying these features with low cost components in an easily assembled design, significant improvement over previous devices has been realized.

The various features of novelty which characterize the invention are pointed out with particularity in the claims annexed to and forming apart of this disclosure. For the better understanding of the invention, its operating advantages, and specific objects attained by its use, reference should be had to the accompanying drawings and descriptive matter in which are illustrated and described preferred embodiments of the invention.

DETAILED DESCRIPTION OF THE PREFERRED EMBODIMENT

Figure 1:
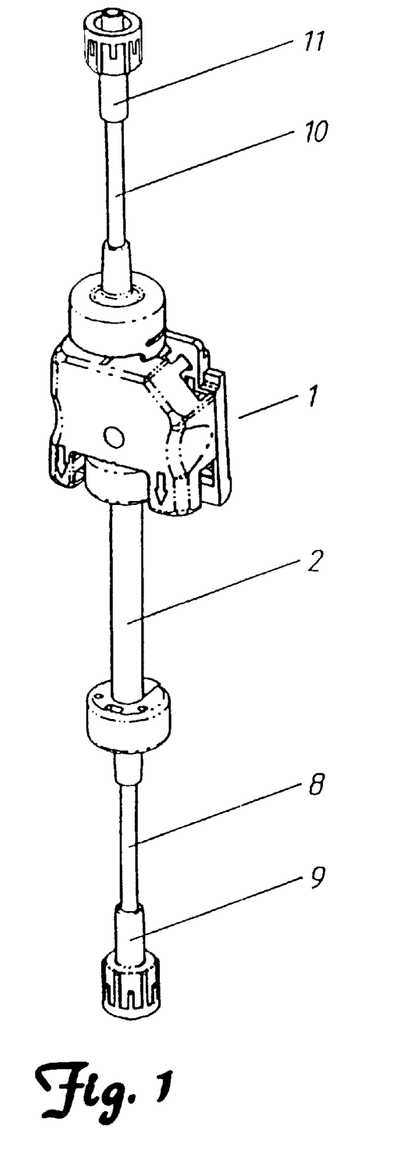
FIG. 1 is a front view of the disposable cassette showing the cassette body, inlet, outlet, and flexible pump tube.

Referring to FIG. 1, a disposable cassette is shown according to the present invention having a cassette body 1 with a flexible pump tube 2 between an inlet tube 8 and inlet connector 9 for connection to a drug reservoir bag (not shown) on the upstream side and an outlet tube 10 and outlet connector 11 for connection to the patient (not shown) on the downstream side.

Figures 2, 3:
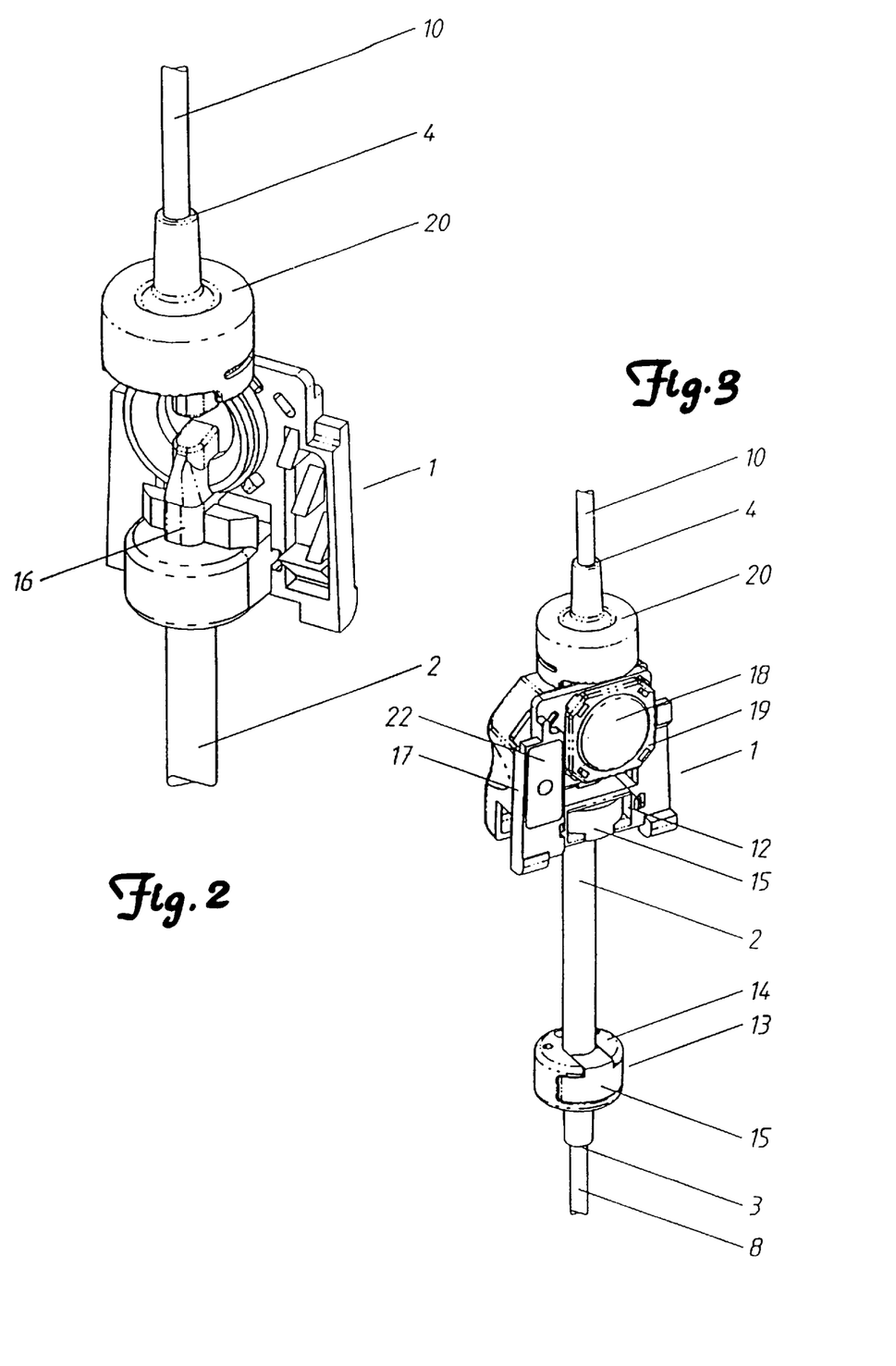
FIG. 2 is a close up of the cassette body with the protective cover removed.
FIG. 3 is a rear view of the cassette body showing additional details.
Figure 4:
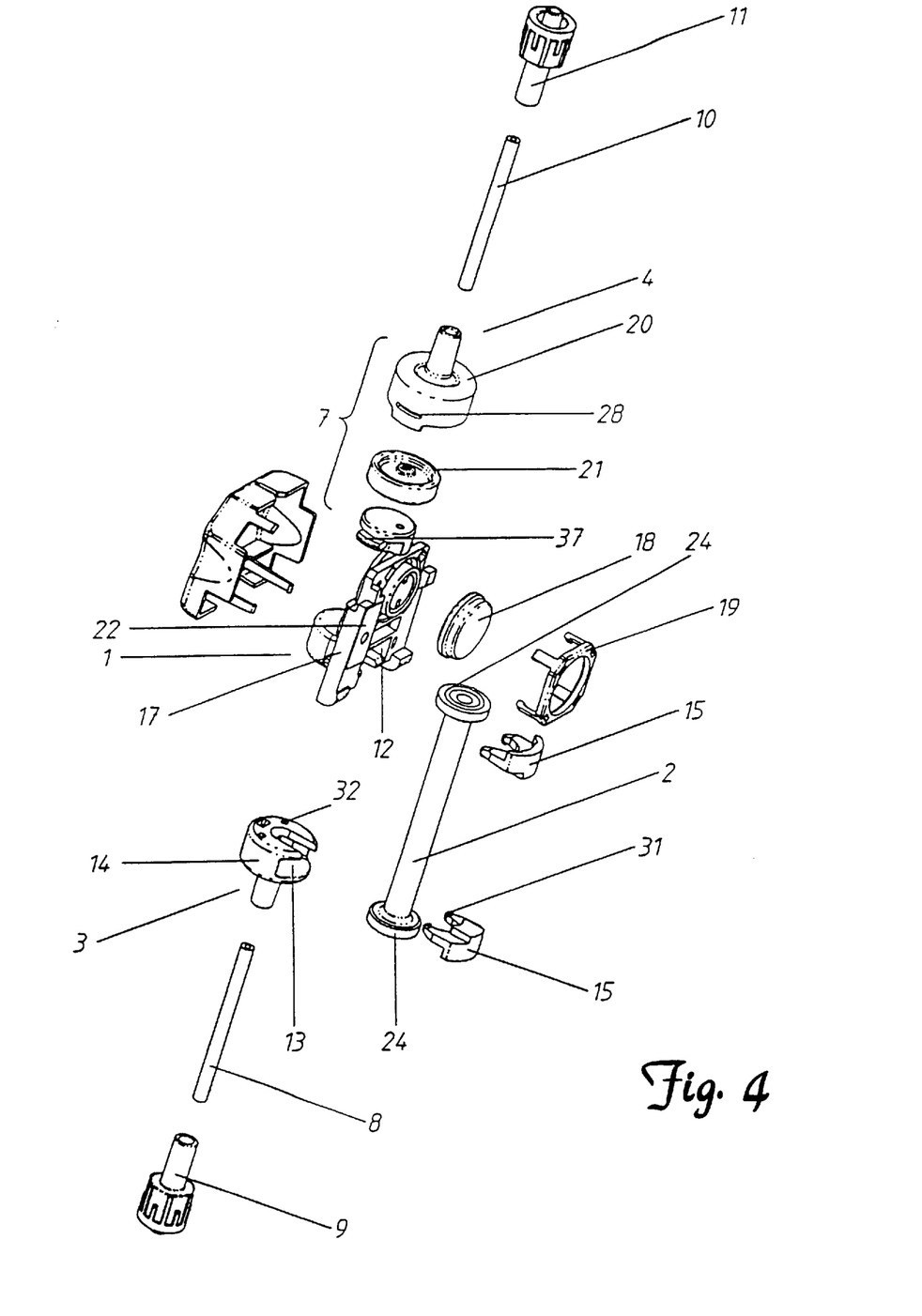
FIG. 4 is an exploded view of the cassette showing the component parts.

The location of the functional components of cassette body 1 are shown in FIG. 2, FIG. 3, and FIG. 4. The cassette body 1 has a compression fitment 12. There is a plastic fitting 14 with a similar compression fitment 13 into which the opposite end of pump tube 2 fits. A compression wedge 15 fits into the fitment areas of both cassette body 1 and plastic fitting 14. The cassette body 1 has an optical air detector 16 and a cassette recognition code 17, both of which are described in more detail below. A pressure detector membrane 18 is mounted into the cassette body 1 and held in place with a snap-fitting ring 19. A valve housing 20 snaps into place on the cassette body 1 and, together with the cassette body 1 and a circular valve membrane 21, forms an anti-freeflow valve 7. This valve 7 is described in more detail below. A label 22 is affixed to the rear side of the cassette body 1 which selectively blocks light paths of the cassette recognition system to form a unique code for different cassettes. Medical grade polyvinyl chloride (PVC) tubing 8 and 10 is bonded into the inlet 3 and outlet 4 and, in turn, into inlet and outlet connectors for the drug reservoir (not shown) and patient connection, respectively.

Figure 5:
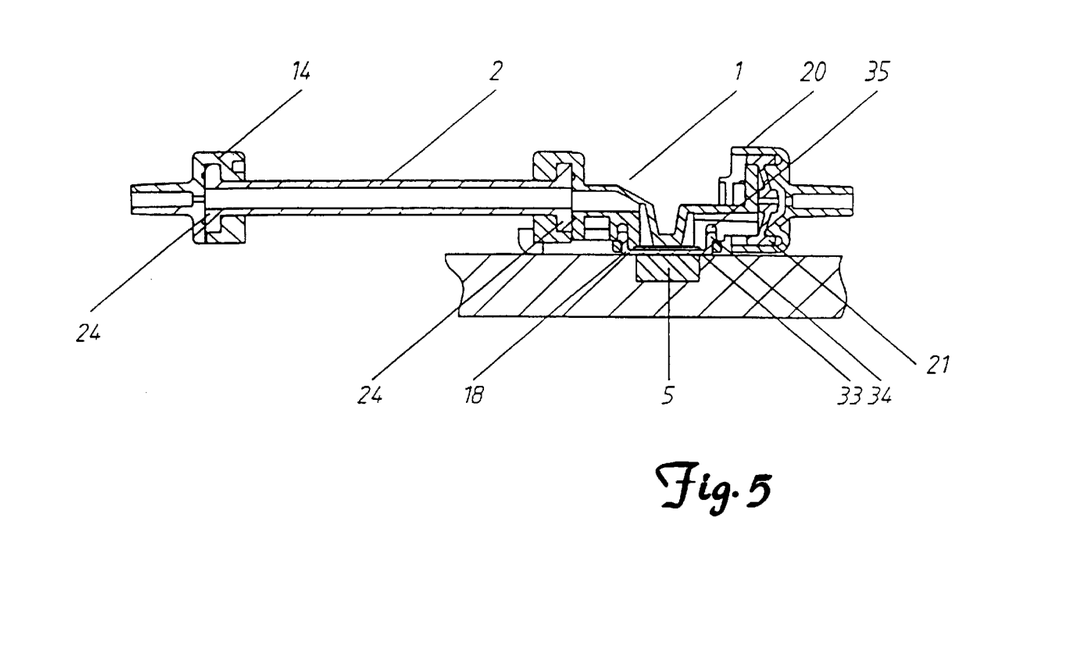
FIG. 5 is a longitudinal cross section of the cassette showing the fluid path and the pressure sensing system.

The pump tube 2 is shown in more detail in FIG. 4. The tube 2 is manufactured using liquid silicone injection molding. The inside diameter is chosen to give the correct volume per cycle of the pump. The wall thickness is chosen to provide adequate recovery of the tube 2 during the fill portion of the pump cycle. Flanges 24 are integrally molded onto each end. These flanges 24 are compressed into appropriate fitments 12 and 13 during assembly of the cassette to produce a leak-free, easily assembled interface between the silicone pump tube 2 and the plastic components. FIG. 5 shows the tube 2 in the assembled position. On one side, the flange 24 is assembled into cassette body 1 and on the other side into a plastic fitting 14 into which flexible PVC tubing 8 (not shown) is bonded. As shown in FIG. 4, the flanges 24 are slid into the fitments 12 and 13, and then compressed and secured with wedges 15 that snap-fit into position. These wedges 15 have hooks 31 that mate with slots 32 in the cassette body 1 and plastic fitting 14.

FIG. 4 shows the pressure detector membrane 18 which is assembled into the cassette body 1 with a snap-fitting ring 19. This membrane 18 is produced as a single liquid silicone injection molded part. FIG. 5 shows the membrane 18 in the functional position. A pressure detector 5 is located in the infusion pump. This combination is used to measure pressure in the fluid and thus occlusion of the infusion line. The pressure detector membrane 18 has a round, thin, flexible face 33 that serves as an isolation interface between the pressure detector 5 of the pump and the sterile fluid path. Because the face 33 is substantially flat in the functional position and because the pressure detector 5 has a relatively high mechanical impedance, the pressure in the fluid line is faithfully transmitted to the pump. The membrane 18 has an integral flange 34 around the outer diameter. This flange 34 compressibly fits into a groove 35 in the cassette body 1 to effect a leak-free seal.

Figure 1A:
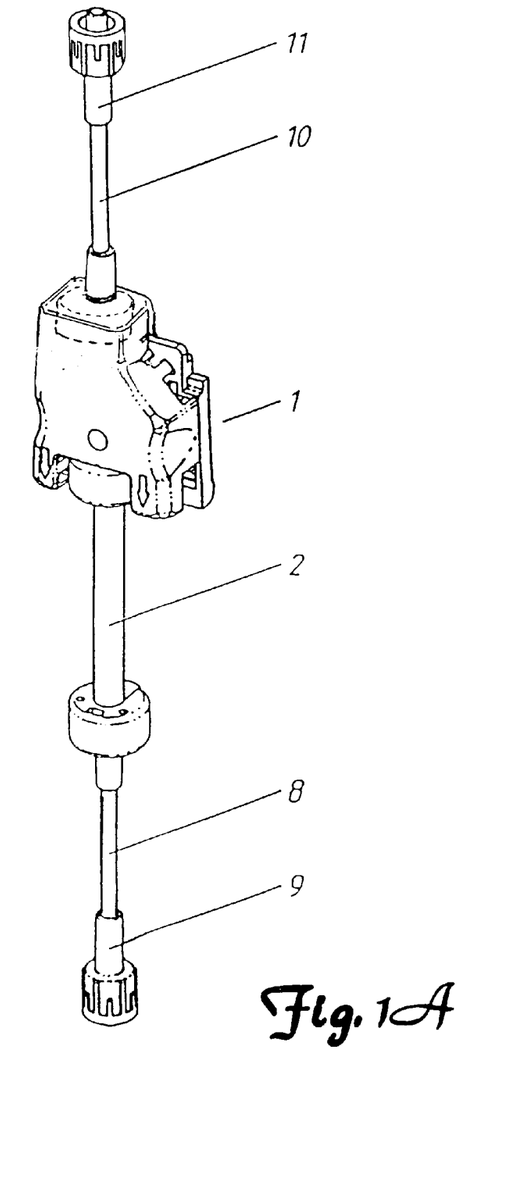
FIG. 1a shows an embodiment of the cassette of the present invention wherein the valve is in the cassette.
Figure 6:
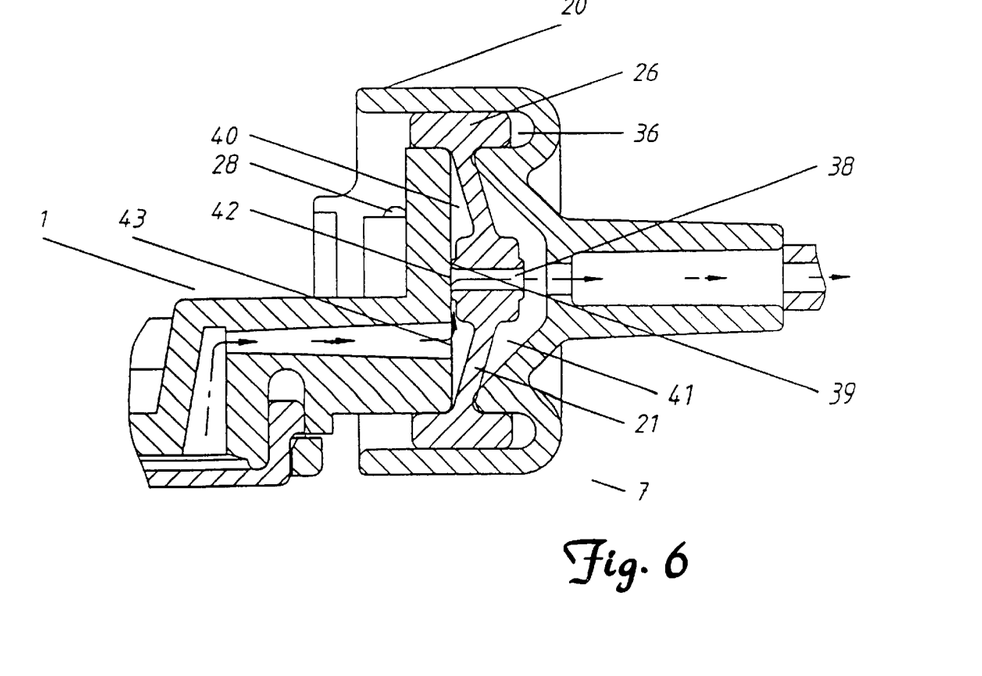
FIG. 6 is a close-up cross section of the passive check valve in the assembled cassette.

FIG. 6 shows the construction of the passive valve 7 that is part of the cassette body 1. The valve 7 is comprised of the cassette body 1, and a valve housing 20, and a circular membrane 21 which is produced as a single liquid silicone injection molded part. The membrane 21 has an integral flange 26 on the outer circumference which compressibly fits into a groove 36 formed between the cassette body 1 and the housing 20 to make a leak-free static seal. The valve housing 20 snap-fits into and is held in proper position by interaction of the wings 37 (FIG. 4) on the cassette body 1 and the slots 28 (FIG. 4) on the valve housing 20. FIG. 1a shows an embodiment of the cassette of the present invention wherein the valve 7 is in the cassette body 1.

The membrane 21 has a center hole 38 as the fluid path and has a seal lip 39 around the circumference of the hole. This lip 39 is the active seal of the valve 7, and operatively mates with the surface of seat 42 of the cassette body 1. The valve membrane 21 has a pre-stress that results in a positive forward opening pressure (called crack pressure). The pre-stress is produced during assembly by axial deflection of the lip 39 by the seat 42. The preferred embodiment has a crack pressure of between 0.15 and 0.5 bar. This range is selected based, on the lower end, on the possible elevation of the drug reservoir above the patient during use, and, on the upper end, by the performance of the infusion pump. This positive crack pressure eliminates the possibility of potentially harmful freeflow to the patient as described in BACKGROUND ART above.

Turning now to the operation of the valve 7 and referring to FIG. 6, when the pressure difference between upstream chamber 40 and downstream chamber 41 is less than the crack pressure, the seal lip 39 remains against the seat 42 with some finite compressive force. As the pressure difference increases, a force is generated equal to the pressure times the effective membrane area. This force would cause a deflection of the membrane 21 in the same direction as the pre-stress. Once the forces are in balance, the lip 39 no longer touches the seat 42 with any substantive force. Any slight increase above this value will result in fluid flow past the lip 39 and seat 42. It is further easily recognizable that any negative pressure differential serves to force the lip 39 more tightly against the seat 42 thus making an effective back-check valve.

The valve 7 has a unique arrangement of the flow path and pressure areas which makes it highly producible, precise, and not prone to failure form sticking and particles. The fluid path inlet 43 is offset from the axial centerline, the fluid path is through a center hole 38 in the membrane 21, and the active seal lip 39 is on the circumference of this hole. This arrangement means that the pressure acting on the membrane 21 acts outside the seal lip 39. The advantage to this construction is that the area over which the pressure differential acts is not inherently defined by the circumference of active seal lip 39. Thus, the ratio of pressure area to seal area can be and is disproportionately large. The result is that the force required to compress the seal lip 39 to make a seal, as well as any secondary seal sticking forces, is small compared to the available force developed from the pressure differential. This advantageous force relationship makes the valve 7 much more responsive and much less susceptible to secondary effects such as sticking, particles, defects, and scratches than the prior art.

Figure 7:
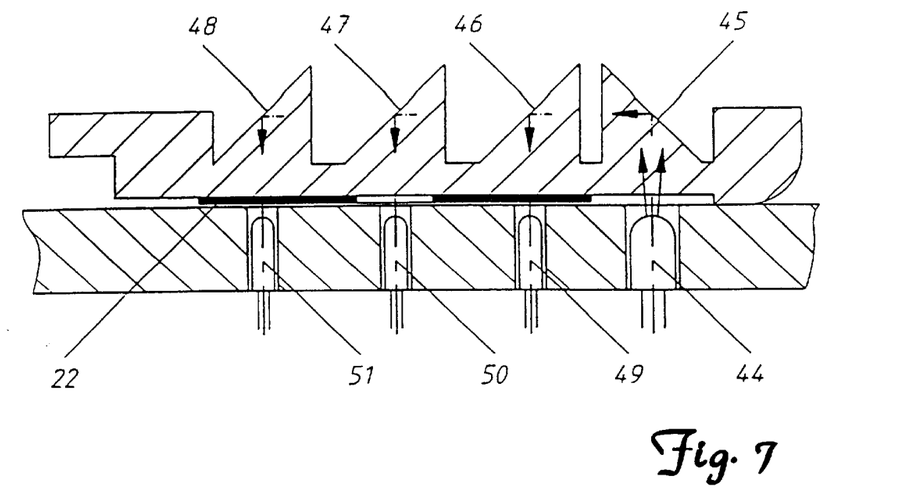
FIG. 7 is a cross section showing the optical elements of the cassette recognition system.

FIG. 7 shows the optical arrangement of the cassette recognition system. Light from the light source 44 in the infusion pump shines outward an is reflected from the main prism 45 towards channel prisms 46, 47, 48 comprising the three channels. These prisms 46, 47, 48 are offset from each other in both the length and depth directions. The light is reflected by prisms 46, 47, 48 back into the infusion pump to three separate light sensors 49, 50, 51. A light blocking label 22 allows light through pre-selected paths thereby generating a binary code. A fail-safe system is assured by using as legitimate only those codes that have equal bit sums. The three unique codes allow the infusion pump to adjust the scale factor for volumetric output per cycle to match to one of three different cassettes. One preferred embodiment has two cassettes which have an output per cycle ratio of 2.5 to 1 from each other. This arrangement allows the flow rate range capability to be substantially broadened without sacrificing continuity of flow for low flow rates or requiring excess power for high flow rates.

Figure 8:
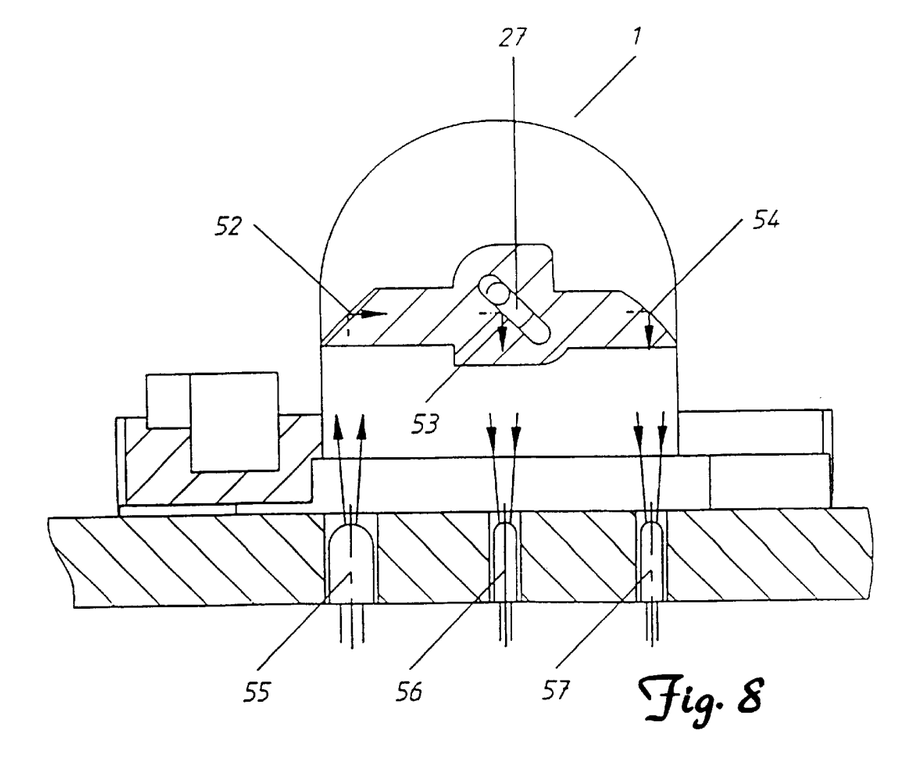
FIG. 8 is a cross section showing the optical elements of the air detector system.

FIG. 8 shows the optical elements of the air detector system. There is a light source 55 in the infusion pump that shines upward into the cassette body 1. The light is reflected and focused by a first prism 52 toward an air detector chamber 27. The air detector chamber 27, through which the liquid medicament flows, has a reflective or transmissive surface 53 for air or liquid, respectively, based on the principles of total reflection or normal refraction, respectively, at a material interface. In the case of air in the chamber 27, the light is reflected back into the infusion pump and to the first light sensor 56. The infusion pump processes this sensor's signal for an air-in-line alarm. For clear liquid in the chamber 27, the light continues toward a second prism 54, or, for opaque fluids, is absorbed in the liquid. For clear fluids the light is reflected and focused from the second prism 54 toward the infusion pump and is read by a second light sensor 57. This arrangement provides a fail-safe design due to the opportunity to detect failures of any of the components because one and only one of the sensors must have a positive signal. For opaque fluids, the air detector channel functions properly, and only the function of the liquid channel is lost.

Referring again to FIG. 5, it is important to note the relative positions of the pump tube 2, pressure detector 5, and valve 7 in the fluid path. Detection of occlusion on the outlet side of the infusion line is easily accomplished by measuring the pressure at the pressure detector 5 and assigning an appropriate trip point.

The situation is much different during occlusion of the inlet side. In this case, during the output portion of the cycle, the fluid can be forced out more our less normally. Therefore, it is important to note that an occlusion on the inlet side will result in an increasing vacuum at the pressure detector 5 during the fill phase because fluid can come neither form the drug reservoir due to the occlusion nor from the patient side due to the back-check action of the valve 7. Also importantly, under normal, non-occluded operation, the positive crack pressure of the valve 7 causes the pressure at the detector 5 to be as great as this crack pressure. This gives differentiable pressure signals between normal operation and inlet side occlusion of at least the crack pressure and a vacuum, respectively. In reality, the pressure detector membrane 18 will move away from the face of pressure detector 5 at negative pressures, so the pressure detector 5 will typically read 0 for a vacuum. Nevertheless, owing to the arrangement of the parts and the accuracy of the pressure detector system, occlusion of the inlet side is easily detectable.

Figure 9:
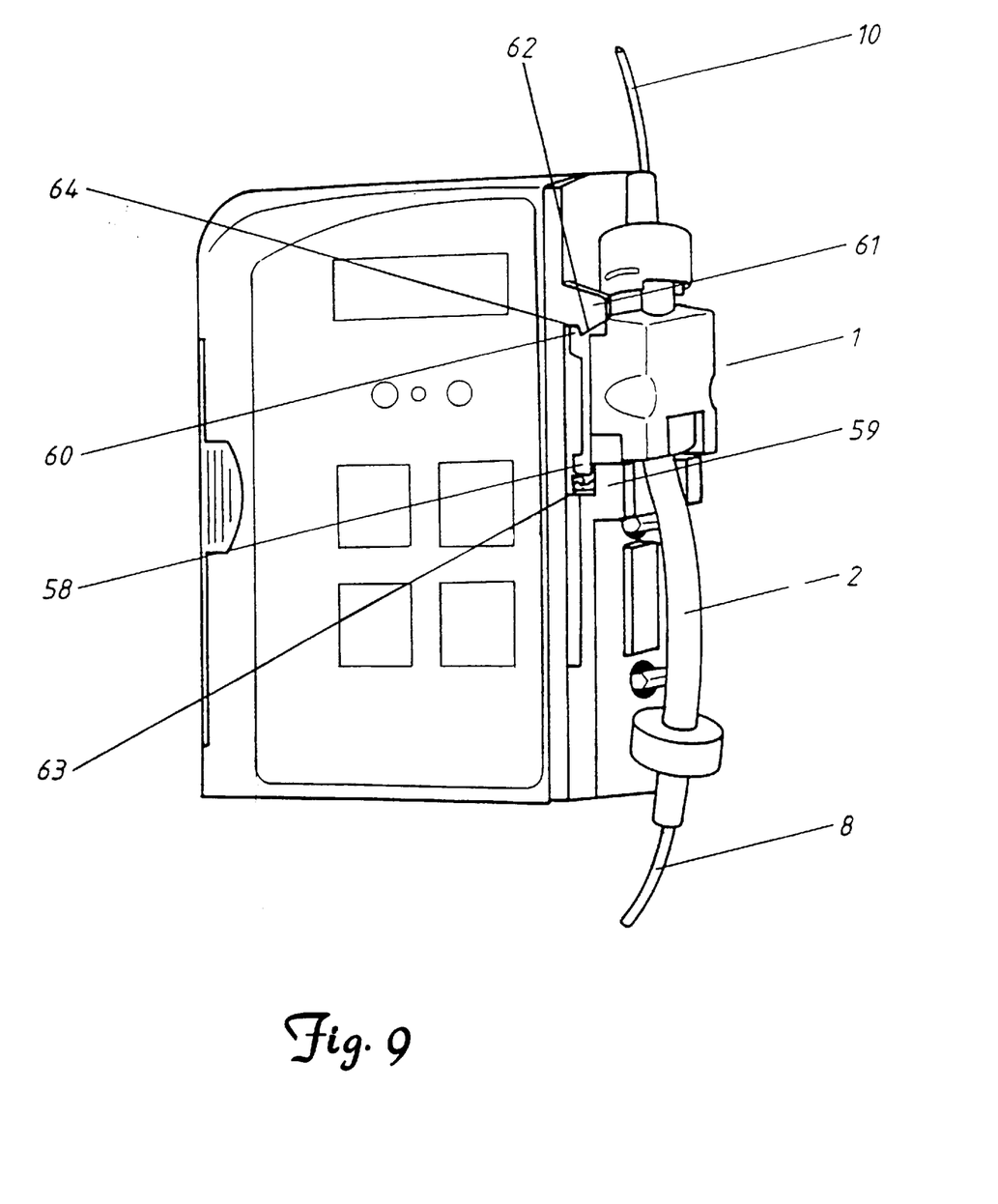
FIG. 9 shows the cassette and pump of the present invention with the cassette properly positioned in the pump.

With reference to FIG. 9, the insertion and positioning to the cassette is performed by first aligning the forward legs 58 of the cassette body 1 with the front hooks 59 of the infusion pump. The rear legs 60 of the cassette body 1 are moved into the proper position by lead-in surfaces 62 on the rear hooks 61 of the infusion pump. This action simultaneously compresses the return springs 63. Once the rear legs 60 and rear hooks 61 align, the return springs 63 force the cassette body 1 into proper operating position. The rear hooks 61 have a slight downward angle 64 to assure proper contact between the pressure detector 5 and the pressure detector membrane 18.

While the foregoing description and drawings represent the preferred embodiments of the present invention, it will be obvious for those skilled in the art that various changes and modifications may be made therein without departing from the true spirit and scope of the present invention.

We claim:

1. Disposable cassette for use with a liquid drug infusion pump, comprising:
   a cassette body with a flexible pump tube having an inlet for connection to a drug reservoir on the upstream side, said cassette body having an outlet for delivery of the drug to a patient on the downstream side;
   a pressure detector membrane operatively connectable to the infusion pump, the pump having means to measure the pressure in the fluid circuit of the cassette;
   a passive valve having a pre-stress producing a forward opening pressure of at least 0.15 bar;
   an optical code located on the cassette body for recognition of the cassette by said infusion pump; and
   an air detector chamber located in the cassette body, said air detector chamber being operably connectable to the infusion pump.

2. Disposable cassette according to claim 1, further comprising means for orienting and holding the cassette in relation to the pump to which it is connectable.

3. Disposable cassette according to claim 2, wherein said passive valve has a pre-stress producing a forward opening pressure between 0.15 and 0.50 bar.

4. Disposable cassette according to claim 2, wherein said passive valve is comprised of a circular membrane with a center hole, the circumference there of operating as an active seal lip.

5. Disposable cassette according to claim 4, wherein said circular membrane has a flange on the outer diameter, said flange forming a static seal.

6. Disposable cassette according to claim 5, wherein said circular membrane is a single injection molded rubber part.

7. Disposable cassette according to claim 2, wherein said passive valve is located in said cassette body.

8. Disposable cassette according to claim 2, wherein the infusion pump includes a pumping mechanism, said flexible pump tube squeezable by said pumping mechanism to produce a peristaltic pumping action.

9. Disposable cassette according to claim 2, wherein said flexible pump tube has integral transverse flanges, said flanges forming compression seals in the assembled cassette.

10. Disposable cassette according to claim 2, wherein said flexible pump tube is made as a single injection molded rubber part.

11. Disposable cassette according to claim 2, wherein said pressure detector membrane has a flange on its outer diameter, said flange comprising a static seal, and further wherein the surface of said pressure detector member is substantially flat, thereby having substantially no effect on the pressure coupling from said cassette to the infusion pump.

12. Disposable cassette according to claim 2, wherein said passive valve prevents back flow, thereby allowing said means to measure the pressure located in said infusion pump to detect an occlusion on the input side of said cassette.

13. Disposable cassette according to claim 2, wherein said optical code is one of a plurality of codes, said code corresponding to a plurality of cassettes each with a different operating number.

14. Disposable cassette according to claim 13, wherein an operating parameter of the pump is a volumetric output per pump cycle and wherein the inside diameter of the tube may be selected to provide a selected volumetric output per pump cycle.

15. Disposable cassette according to claim 2, wherein said air detection chamber includes an optically reflective and transmissive surface for air and liquid, respectively.

16. Disposable cassette according to claim 15, wherein said cassette body includes at least one optically reflective surface for reflecting light from or to said infusion pump.

17. Disposable cassette according to claim 2, wherein said locating means is comprised of a set of hooks, on said infusion pump, a set of plateaux, on said cassette body, mating to said hooks, and a positioning spring action, said spring action reversibly forcing said cassette body into proper position between said hooks and said plateaux.

18. An assembly comprising the disposable cassette according to claim 2 and an infusion pump to which said disposable cassette is connected.

19. Assembly according to claim 18, wherein said means to measure the pressure includes a pressure detector.

20. Assembly according to claim 18, wherein said infusion pump has a light source and at least one light sensor, said source and sensor cooperatively functioning with said air detector chamber to detect the presence of air or liquid and wherein said cassette body includes a surface optically reflective and optically transmissive for air and liquid, respectively.

21. Assembly according to claim 18, wherein said infusion pump has a light source and two light sensors, said cassette body having one reflective surface to reflect light from said source toward said air detector chamber, said chamber having a surface optically reflective and optically transmissive for air and liquid, respectively, said cassette body having a second reflective surface to reflect light transmitted by said surface toward one of said sensors, said reflective or transmissive surface reflecting light toward the other of said two sensors.

22. A disposable cassette for use with a liquid drug infusion pump, comprising:
- a cassette body with an inlet and an outlet and a single, generally linear fluid flow path extending between said inlet and outlet;
- a pressure detector member operably carried by the cassette body generally between the inlet and outlet and operably connectable to a pressure detector associated with the pump; and
- a passive valve with a crack pressure operably carried by the cassette body, said valve generally between the pressure detector member and the outlet.

23. The disposable cassette according to claim 22, wherein said cassette body substantially defines the flow path which extends generally from said inlet, past said pressure detector member, through said valve, and to said outlet, said flow path generally linear, and including at least one offset portion.

24. The disposable cassette according to claim 22, wherein said valve has an inlet and a generally central axis, said inlet offset from said generally central axis.

25. The disposable cassette according to claim 24, wherein said valve comprises a valve housing coupled to the cassette body, said valve housing and cassette body defining a chamber for receiving a valve membrane having an opening generally coaxial with said generally central axis.

26. A disposable cassette for use with a liquid drug infusion pump, comprising:
- a cassette body with a flexible pump tube between an inlet for connection to a drug reservoir and an outlet for delivery of a drug to a patient, said cassette body substantially defining a fluid flow path with an offset region;
- a pressure detector membrane carried by said cassette body and operably connectable to a pressure detector;
- a passive, one way valve carried by said cassette body and having a crack pressure in the direction of the outlet;
- an optical cassette recognition system carried on the cassette body for recognition of the cassette and comprising a plurality of prisms for receiving light from a light source and for reflecting light back to a plurality of sensors, and a light blocking label for creating pre-selected paths of reflected light, thereby identifying the cassette; and
- an air detector chamber associated with the cassette body.

27. The disposable cassette according to claim 26, further comprising means for orienting and holding the cassette in relation to the pump.

28. The disposable cassette according to claim 27, wherein said means for orienting and holding comprises a plurality of hooks carried on the pump and a plurality of legs carried on said cassette body, said legs complementary to said hooks.

29. The disposable cassette according to claim 28, and means for urging said cassette body into proper position with respect to the pump.

30. The disposable cassette according to claim 29, said means for urging comprising at least one spring operably carried by one of the pump and cassette.

31. The disposable cassette according to claim 26, wherein said air detector chamber comprises a surface optically reflective when air is in contact with said surface and optically transmissive when liquid is in contact with said surface.

32. The disposable cassette according to claim 26, wherein said cassette body has one associated reflective surface to reflect light toward said air detector chamber, said chamber having another surface optically reflective when air is in contact with said another surface and optically transmissive when liquid is in contact with said another surface, said cassette body having a second associated reflective surface to reflect light transmitted by said another surface toward a sensors, said another surface reflecting light toward a different sensor.

* * * * *